United States Patent [19]

Yoshikumi et al.

[11] 4,268,505
[45] May 19, 1981

[54] PHARMACEUTICAL COMPOSITION COMPRISING A NITROGEN-CONTAINING POLYSACCHARIDE AND AN ANTIBIOTIC AGENT, AND A METHOD OF TREATING AN INFECTIOUS DISEASE THEREWITH

[75] Inventors: Chikao Yoshikumi, Kunitachi; Yoshio Omura, Tanashi; Tetsuya Hotta, Hoya, all of Japan

[73] Assignee: Kureha Kagaku Kogyo Kabushiki Kaisha, Tokyo, Japan

[21] Appl. No.: 71,482

[22] Filed: Aug. 31, 1979

Related U.S. Application Data

[63] Continuation-in-part of Ser. No. 896,209, Apr. 13, 1978, abandoned.

[51] Int. Cl.³ .............................................. A01K 31/70
[52] U.S. Cl. ........................................ 424/180; 536/1; 536/17 R; 536/18; 424/181
[58] Field of Search .................... 424/180, 181; 536/1, 536/17, 18

[56] References Cited

U.S. PATENT DOCUMENTS

| | | | |
|---|---|---|---|
| 3,436,311 | 4/1969 | Ferguson et al. | 536/1 |
| 3,759,896 | 9/1973 | Komatsu et al. | 536/1 |
| 4,051,314 | 9/1977 | Ohtsuka et al. | 536/1 |
| 4,140,578 | 2/1979 | Yoshikumi et al. | 536/1 |

*Primary Examiner*—Johnnie R. Brown
*Assistant Examiner*—Blondel Hazel
*Attorney, Agent, or Firm*—Wegner & Bretschneider

[57] ABSTRACT

A nitrogen-containing polysaccharide, which is obtainable by extracting mycelia of a fungus belonging to the genus Coriolus of Polyporaceae of Basidiomycetes with an aqueous solvent, is effectively used in treating a bacterial infectious disease due to the strain of the pathogenic bacterial species, which has come to be resistant to the treatment with conventional antibiotics.

15 Claims, 6 Drawing Figures

PHARMACEUTICAL COMPOSITION COMPRISING A NITROGEN-CONTAINING POLYSACCHARIDE AND AN ANTIBIOTIC AGENT, AND A METHOD OF TREATING AN INFECTIOUS DISEASE THEREWITH

CROSS-REFERENCE TO RELATED APPLICATION

The present application is a continuation-in-part of application Ser. No. 896,209, filed Apr. 13, 1978, now abandoned and entitled "USE OF A NITROGEN-CONTAINING POLYSACCHARIDES FOR PROMOTING DRUG-SENSITIVITY OF BACTERIA RESISTANT TO ANTIBIOTICS".

BACKGROUND OF THE INVENTION

This invention relates to use of a nitrogen-containing polysaccharide for treating bacterial infectious disease due to strains of pathogenic bacterial species, which have become resistant to conventional antibiotics.

Advancement of the chemotherapeutical techniques and, particularly, development of a variety of antibiotics have realized a drastic reduction of bacterial infectious diseases such as tuberculosis, dysentery, etc. However, these achievements have invited, on the other hand, a rapid increase of the so-called drug-resistant bacterial strains which defy the existing chemotherapeutics. To make the matter worse, many "multiple-drug-resistant bacteria", that is, strains of bacteria resistant to two or more kinds of drugs, have developed in the serious bacterial genera such as Mycobacteria, Shigella, Staphylococci, etc., and these newcomers are posing a serious problem in the field of chemotherapy against such infectious diseases.

For such reasons, antibiotic preparations usually have a short life cycle and hence the drug manufacturers are compelled to market new kinds of antibiotics one after another in rapid succession at an enormous cost. This can result in a huge loss which cannot be ignored from the viewpoint of social economy.

BRIEF SUMMARY OF THE INVENTION

With the aforesaid situation in mind, we have pursued the extensive studies on the drug-resistant bacterial strains and, as a result, found that the use of a specific nitrogen-containing polysaccharide in combination with an antibiotic can bring about a striking enhancement of drug sensitivity of the strains which have become resistant to the antibiotic. It was also found that the nitrogen-containing polysaccharide is able not only to enhance the potency of the antibiotic against the resistant strain but also expands its effect to allow long-time use of the antibiotics with unchanged effect.

Thus, an object of this invention is to provide a new use of the nitrogen-containing polysaccharide is not only treating, in combination with antibiotics, the bacterial infectious disease due to the bacterial strains which have become resistant to the conventional antibiotics by utilizing the promoted medical antibiotic sensitivity of bacterial strains that have become resistant to antibiotics, but in increasing the potency of the antibiotics against the bacteria while expanding the effect of the antibiotic.

Other objects of this invention will become apparent from the following detailed description of the invention.

DETAILED DESCRIPTION OF THE INVENTION

Figure 1:
FIG. 1 is an infrared absorption spectrum of the nitrogen-containing polysaccharide (NP) of this invention.

The invention will be described in detail hereinbelow. The nitrogen-containing polysaccharide which is used as one of the active components of the agent according to this invention is obtainable by extracting mycelia of a fungus belonging to the genus Coriolus of Polyporaceae of Basidiomycetes with an aqueous solvent. The term "mycelia of a fungus belonging to the genus Coriolus of Polyporaceae of Basidiomycetes" as herein used is based on the classification in "Coloured Illustration of Fungi of Japan" by Rokuya Imazeki and Tsugio Hongo (Hoikusha Pub. Co.).

The method of obtaining the nitrogen-containing polysaccharide used as one of the active components in this invention is briefly described below.

The mycelia of a fungus belonging to the genus Coriolus, which are used as the starting material for the extraction process can be produced either naturally or by artificial culture. In cases of artificially culturing the fungi by using a liquid culture medium, it is possible to use as the starting material all the cultured product including not only the product mycelia but also the eluate in the liquid medium after culture. The thus obtained starting material is extracted with an aqueous solvent and the extract is subjected to suitable treatments such as filtration, neutralization, concentration of the filtrate, dialysis, salting-out, etc. to remove the low-molecular material (with molecular weight of lower than 5,000) from the extract, and is dried to obtain a powdery substance. The thus obtained powdery substance is composed of a nitrogen-containing polysaccharide and can be used as one of the active components in this invention.

The nitrogen-containing polysaccharide obtained in the manner described above has the following properties.

Physiochemical properties (1) General

The substance is powdery in form and brown in color, shows no definite melting point and is carbonized when strongly heated. It is insoluble in the organic solvents such as pyridine, chloroform, benzene, hexane, etc., but soluble in water.

(2) Infrared absorption spectrum

The infrared absorption spectrum of this substance indicates absorption at and in the vicinity of 3,600–3,200 $cm^{-1}$, 2,920–2,900 $cm^{-1}$, 1,660–1,610 $cm^{-1}$, 1,460 $cm^{-1}$, 1,410 $cm^{-1}$, 1,360 $cm^{-1}$, 1,230 $cm^{-1}$, 1,150 $cm^{-1}$, 1,080 $cm^{-1}$, 1,060–990 $cm^{-1}$, 925 $cm^{-1}$, 890 $cm^{-1}$, 840 $cm^{-1}$, 755 $cm^{-1}$ and 705 $cm^{-1}$. Thus, there are noted absorption by $\beta$-bonds of glucan in the saccharide portion at 890 $cm^{-1}$ and another absorption by $\alpha$-bonds of glucan at 840 $cm^{-1}$.

(3) Elementary analysis

The composition of the substance, as measured by an elementary analysis, comprises 42 to 46% of carbon, 5.3 to 7.0% of hydrogen and 0.5 to 8.0% of nitrogen. The balance is oxygen.

(4) Optical rotation

The optical rotation of the substance, as determined in terms of the specific rotatory power $[\alpha]_D^{25}$ is 0 to +50.

(5) Color reaction

The substance is positive in the phenol-sulfuric acid reaction, anthrone-sulfuric acid reaction and ninhydrin reaction. The positive disposition in these color reactions indicates that the active substance used in this invention is composed of saccharide and protein. In order to determine the saccharide composition of the nitrogen-containing polysaccharide, a sample was hydrolyzed with a methanolic solution of hydrochloric acid and, after trimethylsilylation by a known method, subjected to gas chromatography. The result showed that said substance is mainly composed of glucose and also contains small amounts of mannose, galactose, xylose and fucose. An amino acid analysis of the protein portion of the nitrogen-containing polysaccharide revealed that the protein portion of the substance is composed of aspartic acid, threonine, serine, glutamic acid, proline, glycine, alanine, cystine, valine, methionine, isoleucine, leucine, tyrosine, tryptophan, phenylalanine, lysin, histidine, and alginine. Predominant among them are aspartic acid, threonine, glutamic acid, glycine, alanine, valine and leucine, and they account for more than 70% of the entire amino acids.

(6) Proton nuclear magnetic resonance spectrum (NMR)

An NMR absorption spectroscopy was carried out for determining the ratio between the saccharide and protein portions in the nitrogen-containing polysaccharide as well as the saccharide bonds therein.

Figure 2:
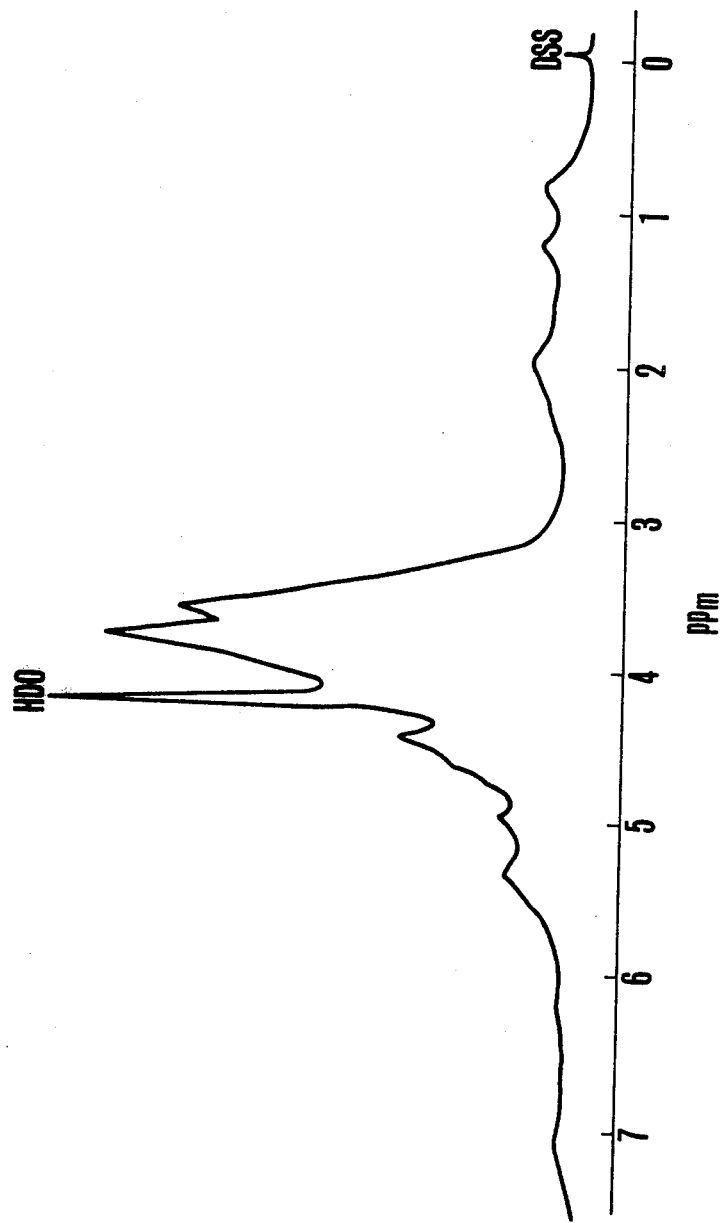
FIG. 2 is a proton nuclear magnetic resonance absorption spectrum (N.M.R.) of the substance.

The NMR absorption spectrum of the sample was measured at 100 MHz by using heavy water as the solvent and sodium 2,2-dimethyl-2-silanopentane-5-sulfonate (D.S.S.) as internal standard. As shown in FIG. 2, absorptions are note at $0.9\pm0.2 - 1.2\pm0.2$ ppm, $2.0\pm0.2$ ppm, $4.5\pm0.2$ ppm, $4.7\pm0.2$ ppm, $5.0\pm0.2$ ppm and $5.4\pm0.2$ ppm, respectively, and a broad absorption band is seen at 3.0–4.4 ppm. The protein portion was examined by assuming that the region of 0.5–2.5 ppm is associated with proton intensity of the protein portion and the region of 2.5–6.0 ppm is associated with proton intensity of saccharide. The protein portion was estimated less than 40%. Also assuming that the region of 4.4–4.9 ppm is associated with $\beta$-bonds of saccharide and the region of 4.9–5.4 ppm is associated with $\alpha$-bonds, their ratio ($\beta/\alpha$) was determined to be within the range of 85/15 to 40/60.

(7) Molecular weight

The molecular weight of the nitrogen-containing polysaccharide in this invention, as measured by ultracentrifugation, was within the range of 5,000 to 300,000.

Acute toxicity

The test was made on the mice of ICR-JCL strain, 4 to 5-week old, weighing 21 to 24 g and the rats of Donryu strain, 4 to 5-week old, weighing 100 to 150 g. The substance dissolved in a physiological salt solution was administered via the following four routes: intravenous, subcutaneous, intraperitoneal and oral. The general symptoms, the death and the change of body weight of the test animals were observed for the period of 7 days, and thereafter they were killed and autopsied. As a result, no case of death was seen in both rats and mice even at the highest dose as shown in Table 1 below. Determination of $LD_{50}$ was practically impossible because none of the animals died in the experiment.

TABLE 1

| Animal | Route of administration | $LD_{50}$ (mg/kg) | |
| --- | --- | --- | --- |
| | | Female | Male |
| Mouse | Intravenous | >1,300 | >1,300 |
| | Subcutaneous | >5,000 | >5,000 |
| | Intraperitoneal | >5,000 | >5,000 |
| | Oral | >20,000 | >20,000 |
| Rat | Intravenous | >600 | >600 |
| | Subcutaneous | >5,000 | >5,000 |
| | Intraperitoneal | >5,000 | >5,000 |
| | Oral | >20,000 | >20,000 |

We will now describe the effect of the nitrogen-containing polysaccharide (hereinafter referred to simply as the present substance) promoting the drug-sensitivity of the drug-resistant strains of bacterial species, which have become resistant of the antibiotics.

The antibiotics which exhibit their effect against the drug-resistant strains of bacterial species when combined with the present substances are those derived from molds, bacteria, actinomyces and the like, and typical examples of such antibiotics are as listed below:
Penicillin G (hereinafter abbreviated as PG)
Streptomycin (hereinafter abbreviated as SM)
Kanamycin (hereinafter abbreviated as KM)
Chlorampheniocol (hereinafter abbreviated as CP)
Tetracycline (hereinafter abbreviated as TC)
Erythromycin (hereinafter abbreviated as EM)
Aminobenzylpenicillin (hereinafter abbreviated as AP)
Cephaloridine (hereinafter abbreviated as CE)
Colistin (hereinafter abbreviated as CL)

The present substance produces the effect in promoting the drug-sensitivity of the following drug-resistant strains of bacterial species to the antibiotics:
*Escherichia coli*
*Streptococcus faecalis*
*Staphylococcus aureus*
*Enterobacter aerogenes*
*Salmonella enteritidis*
*Shigella Sonnei*
*Klebsiella pneumoniae*
*Proteus mirabilis*
*Pseudomonas aeruginosa*

The effect of the present substance in promoting drug sensitivity of the drug-resistant strains of bacterial species was confirmed in the following way.

The drug-resistant strains of bacterial species were obtained in the manner described below according to the concentration gradient plate culture (see "Chemotherapeutics and Resistant Bacteria", 1970, By Chikara Watanabe, Asakura Shoten).

The agar plates with drug concentration gradient ranging from 10 to 100 µg/ml were prepared, and each strain of the bacterial species to be tested was streaked or smeared. These plates were kept at 37° C. for several days and the colony formed in the high concentration area was isolated and again similarly inoculated to the plates. Such operation was repeated several times to obtain the bacterial strains resistant to the respective drugs.

The drug sensitivity of the drug-resistant strains and that of the original strains (sensitive strains) were compared by way of the minimum growth inhibiting concentration (hereinafter abbreviated as MIC) according to the Standard Method of the Japanese Chemotherapeutical Association (see "Chemotherapy" Vol. 22, No. 6, 1126 (1974), by MIC Determination Method Reform Committee). More specifically, double diluted systems of each drug were prepared and they were mixed with the heart-infusion agar medium (Nippon Eiyo Kagaku Co., Ltd.) to form the agar plates. Then a loopful of each strain, which had been cultured at 37° C. in Trypto-soy bouillon (Nippon Eiyo Kagaku Co., Ltd.) for 18 hr. was smeared on each the plate, and after culturing for 18 hr. at 37° C., the growth of the strain on each plate was examined.

In order to see the change of MIC for each resistant strain by the combined use of the present substance and the antibiotics (those which have lost their effect on the bacterial strains), the same procedure was carried out as above except for admixing, in addition, of 10 to 1,000 $\mu$g/ml of the present substance into the systems and the MIC value was determined according to the aforementioned agar plate method.

MIC has apparently been reduced to half the level or less before addition of the present substance as will be seen in Table 3 of EXAMPLE 1. The amount of the present substance added is more than 10 $\mu$g/ml, preferably more than 100 $\mu$g/ml. The pH of the medium was maintained at 7.2±0.1 so that MIC would not be affected by pH of the medium. Also, it was previously ascertained by the agar dilution culture method that the present substance per se has no antibacterial activity against the bacterial strains tested.

Therapeutical test for bacterial infectious diseases

The therapeutical test for infectious disease was carried out in the following way.

A mouse was intraperitoneally inoculated with, for instance, $1 \times 10^8$ cells of the drug-resistant strain of a bacterial species, and 1 to 3 hours later, 10 to 1,000 mg/kg (body weight of mouse) of an antibiotic and 1 to $10^4$ mg/kg of present substance were administered either intraperitoneally or orally. Daily observation was continued for 7 days after the administration to examine the rate of survival for evaluating the effectiveness of the present substance. In this case, it was found that the effective dosage of the present substance was preferably over 10 mg/kg for intraperitoneal administration and over 100 mg/kg for oral administration.

The effectiveness in this therapeutical treatment is evaluated by comparing the rate of survival of the group (1) of mice inoculated and subjected to the combined treatment with the present substance, i.e., a nitrogen-containing polysaccharide and an antibiotic with that of the group (2) of mice inoculated and subjected to the administration of only the above-mentioned antibiotic. That is, in the case where the number of mice of a group is ten and the number of mice surviving on 7th day of the test is eight in the group (1) and five in the group (2), the effectiveness of the treatment of the present invention is denoted as follows:

8/5=1.6: This treatment was 1.6 times effective over the conventional treatment. The actual effectiveness of the combined treatment of the present substance and an antibiotics is, as is seen in Examples, 1.6 to 2.3 times over the treatment with only the antibiotic.

Thus, it was ascertained that the present substance is capable of enhancing the antibacterial effectiveness of an antibiotic not only in in vitro application but also in chemotherapy of the bacterial infectious diseases tested.

The present substance also shows an extremely low acute toxicity and it can be administered in various ways, such as intraperitoneal injection, dermal administration, oral administration and intrarectal administration. Thus, the present substance may be mixed with an antibiotic in the course of drug preparation or may be administered separately with the administration of the antibiotic.

When the substance is prepared into tablets, granules, powder, capsules or the like for oral administration, the composition of any such preparation may contain an additive of the type generally used in drug preparation, such as binding agent, inclusion agent, excipient, lubricant, disintegrator, wetting agent, etc. When the substance is used as a liquid for oral administration, it may be prepared into the form of an internal liquid medicine such as shake mixture, suspension, emulsion, sirup, etc., or it may be prepared into the form of a dry product which is re-dissolved just before use. Such liquid preparations may also contain the additives and/or preservative of the type usually used for drug preparations. The injections may contain additives such as a stabilizer, buffer, preservative, isotonizer, etc., and may be supplied in the form of unit dose ampoules or multiple dose containers. Also, the above-mentioned compositions may be provided in the form of an aqueous solution, suspension, solution or emulsion in an oil or aqueous vehicle, while the active components may be given in the form of a powder which is redissolved with a suitable vehicle, for example sterilized pyrogen-free water, just before use. In case the substance is used in the form of an ointment or inunction, it may contain an oil or fat base, emulsive base, water-soluble base, preservative or the like.

EXAMPLE 1

Preparation of nitrogen-containing polysaccharide

A liquid culture medium of the following composition was prepared:

| | |
|---|---|
| Peptone | 5 g |
| Yeast extract | 3 g |
| $KH_2PO_4$ | 0.3 g |
| $K_2HPO_4$ | 0.3 g |
| $MgSO_4 . 7H_2O$ | 0.3 g |
| Glucose | 50 g |
| Water | 1 liter |
| pH: 6.0 | |

An aliquot of 150 ml of this medium was introduced into each of 100 conical flasks of capacity of 1 l, and after sealing each flask with cotton plug, the liquid culture medium was subjected to sterilization for 30 min. at 120° C. and then inoculated in a usual wayy with the separately slant-cultured mycelia of the strain CM 105 of *Coriolus versicolor* (Fr.) Quél. (Deposit No. FERM-P-2416*) followed by 20-day stationary culture at 25° to 27° C. The thus obtained culture slurry (broth) was dried by a double-drum type drum-dryer to obtain 451 g of a dry product. One hundred and fifty grams of this dry product was crushed and extracted with an aqueous 0.1 N sodium hydroxide solution at a temperature of 95° to 98° C. and under normal pressure for 3 hr. by using a stainless extractor. The thus obtained alkaline extract solution was neutralized and filtered and then the filtrate was concentrated to 500 ml. This concentrated solution and then encapsulated in a cellophane film and subjected to dialysis in running water for 90 hr.

Note: *Deposited in the Fermentation Research Institute, Agency of Industrial Science and Technology, Ministry of International Trade and Industry, Chiba-shi, Japan.

The obtained dialyzate was concentrated under reduced pressure and spray-dried to obtain 19.5 g of powdery product.

In order to examine the properties of this powdery product, a sample thereof was subjected to an elementary analysis, the result showing 42.1% of carbon, 6.9% of hydrogen and 5.8% of nitrogen. Determination of specific rotary powder was carried out on a 0.25% aqueous solution of the sample. The result showed the specific rotatory power of this product is $+12°$.

In order to determine the saccharide composition of the product, 10 mg of the sample was added to a 3% methanolic solution of hydrochloric acid to perform methanolysis for 16 hr. at 100° C. The reactant was filtered after neutralizing the hydrochloric acid with silver carbonate at room temperature, and the obtained filtrate was concentrated and evaporated to dryness. The solid product was then dissolved in 0.5 ml of pyridine and further mixed with 0.2 ml hexamethyldisilazane and 0.3 ml of trimethylchlorosilane, the mixture being allowed to stand at room temperature for 30 min. to effect trimethylsilylation. The product was then dissolved in chloroform, and after washing away the excess reagent and dehydrating, the filtrate was evaporated to dryness. This product was then dissolved in carbon tetrachloride and subjected to gas chomatography. The result showed the composition comprising 70.5% of glucose, 3.8% of galactose, 10.3% of mannose, 5.4% of xylose and 10.0% of fucose.

For determining the protein composition of the powdery product, a sample thereof was subjected to an amino acid analysis according to a normal method. The result showed the following composition: 15% of aspartic acid, 8% of threonine, 6% of serine, 14% of glutamic acid, 4% of proline, 8% of glycin, 10% of alanine, 4% of isoleucine, 6% of leucine, 1% of tyrosine, 4% of phenylalanine, 25 of tryptophan, 2% of lysin, 3% of alginine, 4% of ammonia and 1% N-glucosamine, and a trace of histidine.

As for NMR absorption, heavy water was used as a solvent while employing sodium 2,2-dimethyl-2-silanopentane-5-sulfonate as an internal standard, and in order to eliminate any possible influence of residual light water in heavy water, there were used the values which has undergone correction that was made based on the presumed Lorenz's curve. Under these conditions, the ratio of saccharide portion to protein portion was determined by assuming that absorption at 0.5–2.5 ppm is due to proton in the protein portion and absorption at 2.5–6.0 ppm is due to proton in the saccharide portion. The obtained ratio of saccharide to protein was 89/11. Also, the ratio of $\beta$-bonds to $\alpha$-bonds was determined by assuming that an absorption band at 4.4–4.9 ppm is associated with $\beta$-bonds of saccharide and an absorption band at 4.9–6.0 ppm is associated with $\alpha$-bonds. Such ratio was 65/35.

The molecular weight was determined by means of ultracentrifugation, and it was carried out by employing the sedimentation equilibrium and synthetic boundary pattern utilizing an interference optical system under the following conditions: concentration of sample of 0.3%, solvent of M/10 KCl; temperature of 25° C.; liquid column of 1.7 mm; and rotation of 22,000 r.p.m. with a measuring time of 5 hr.

The obtained average molecular weight was 100,000. Test of the effect of promoting the drug-sensitivity of the drug-resistant bacterial strain which has become resistant to antibiotics:

(1) Preparation of a drug-resistant bacterial strain

Specimens of the drug-resistant bacterial strain were obtained according to the aforementioned concentration-gradient plate culture by using Staphylococcus aureus, Streptococcus faecalis, Escherichia coli, Salmonella enteritidis, Klebsiella pneumoniae and Pseudomonas aeruginosa. The MICs of the original bacterial strains and those of the bacterial strains which have developed resistance to the respective antibiotics are summarized in Table 2.

TABLE 2

| Bacteria | Antibiotics | Minimum growth inhibiting concentration. MIC ($\mu$g/ml) | |
|---|---|---|---|
| | | Original strain | Resistant strain |
| Staphylococcus aureus | PG | 0.025 | 12.5 |
| | CP | 3.1 | 25 |
| | TC | 0.8 | 25 |
| | EM | 0.4 | 12.5 |
| | SM | 1.6 | 100< |
| Streptococcus faecalis | TC | 0.4 | 25 |
| Escherichia coli | PG | 12.5 | 100< |
| | SM | 3.1 | 100 |
| | KM | 6.3 | 200 |
| | CP | 1.6 | 50 |
| | TC | 3.1 | 25 |
| | CE | 3.1 | 25 |
| | EM | 100< | — |
| Enterobacter aerogenes | KM | 3.1 | 100 |
| Salmonella enteritidis | PG | 6.3 | 100< |
| | CP | 0.8 | 12.5 |
| | SM | 25 | 100< |
| | TC | 1.6 | 12.5 |
| | EM | 100< | — |
| Shigella sonnei | KM | 3.1 | 50 |
| Klebsiella pneumoniae | PG | 6.3 | 100< |
| | SM | 1.6 | 100 |
| | CP | 0.8 | 25 |
| | TC | 1.6 | 25 |
| | EM | 12.5 | 100< |
| Proteus mirabilis | AP | 0.8 | 25 |
| Pseudomonas aeroginosa | CL | 12.5 | 200 |

Notes:
The MIC values of PG were calculated on the assumption that 1,667 U (units) = 1 mg;
The MIC values of CL were calculated on the assumption that 30,000 U (units) = 1 mg (2) Effect of promoting the drug-sensitivity of the drug-resistant bacterial strains:

In order to see the change of MIC value of the respective drug-resistant strains by joint use of the present substance and various antibiotics (those used for providing the bacterial strain with resistance), the present substance was added to the culture medium in amounts of 10 to 1,000 $\mu$g/ml and the MIC values were obtained from the agar plate method. The results are shown collectively in Table 3.

TABLE 3

| Resistant strain of bacteria | Drug (antibiotics) | Concentration of present substance ($\mu$g/ml) | Minimum growth Inhibiting concentration ($\mu$g/ml) | |
|---|---|---|---|---|
| | | | Not-added** | Added* |
| Staphylococcus aureus | | | | |
| PG-resistant | PG | 1000 | 12.5 | 1.6 |
| CP-resistant | CP | 100 | 25 | 6.3 |

TABLE 3-continued

| Resistant strain of bacteria | Drug (antibiotics) | Concentration of present substance (μg/ml) | Minimum growth Inhibiting concentration (μg/ml) Not-added** | Added* |
|---|---|---|---|---|
| TC-resistant | TC | 100 | 25 | 3.2 |
| EM-resistant *Streptococcus faecalis* | EM | 1000 | 12.5 | 3.2 |
| TC-resistant *Escherichia coli* | TC | 100 | 25 | 6.3 |
| SM-resistant | SM | 1000 | 100 | 25 |
| KM-resistant | KM | 1000 | 200 | 50 |
| CP-resistant | CP | 100 | 50 | 12.5 |
| TC-resistant | TC | 100 | 25 | 6.3 |
| CE-resistant *Enterobacter aerogenes* | CE | 10 | 25 | 12.5 |
| KM-resistant *Salmonella enteritidis* | KM | 1000 | 100 | 12.5 |
| CP-resistant | CP | 100 | 12.5 | 3.2 |
| TC-resistant *Klebsiella pneumoniae* | TC | 100 | 12.5 | 6.3 |
| SM-resistant | SM | 1000 | 100 | 25 |
| CP-resistant | CP | 100 | 25 | 6.3 |
| TC-resistant *Shigella sonnei* | TC | 100 | 25 | 12.5 |
| KM-resistant *Proteus mirabilis* | KM | 1000 | 50 | 12.5 |
| AP-resistant *Pseudomonas aeruginosa* | AP | 10 | 25 | 12.5 |
| CL-resistant | CL | 1000 | 200 | 100 |

Notes:
*The present substance was added to the culture medium
**The present substance was not added to the culture medium

EXAMPLE 2

Figure 3:
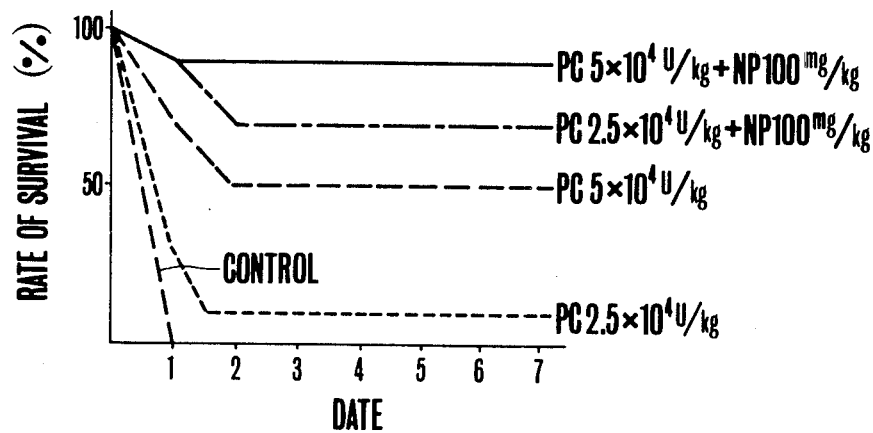
FIGS. 3 to 6 are the graphs showing the effects according to the present invention.

A therapeutical test for a bacterial infectious disease was carried out on five groups of male ICR-JCL mice (each weighing 22±1 g), each group consisting of 10 mice, by using the penicillin G-resistant strain of *Staphylococcus aureus* obtained in Example 1. The penicillin G-resistant strain of *Staphylococcus aureus* which had been cultured in a Trypto-soy agar medium (Nippon Eiyo Kagaku Co., Ltd.) at 37° C. for 18 hr. were suspended in a Trypto-soy bouillon (Nippon Eiyo Kagaku Co., Ltd.) containing 5% of mucin, and 0.25 ml of such suspension was intraperitoneally inoculated to each mouse. The inoculum was controlled to be $5 \times 10^8$ bacterial cells per mouse. Two hours after the inoculation, penicillin G was intraperitoneally administered at the dose of $2.5 \times 10^4$ U/kg (body weight of mouse) and $5 \times 10^4$ U/kg, respectively, while the present substance obtained according to the process of Example 1 was also intraperitoneally administered at the dose of 100 mg/kg (body weight of mouse). The thus treated mice were observed every day for the period of 7 days after the administration, and the rate of survival of the inoculated mice was determined. The results are shown in FIG. 3. It was proved by these results that the combined use of the present substance, the nitrogen containing polysaccharide (NP), can improve the remedial effect of penicillin G while raising the sensitivity to penicillin G of the resistant bacterial strain in vivo.

EXAMPLE 3

Figure 4:
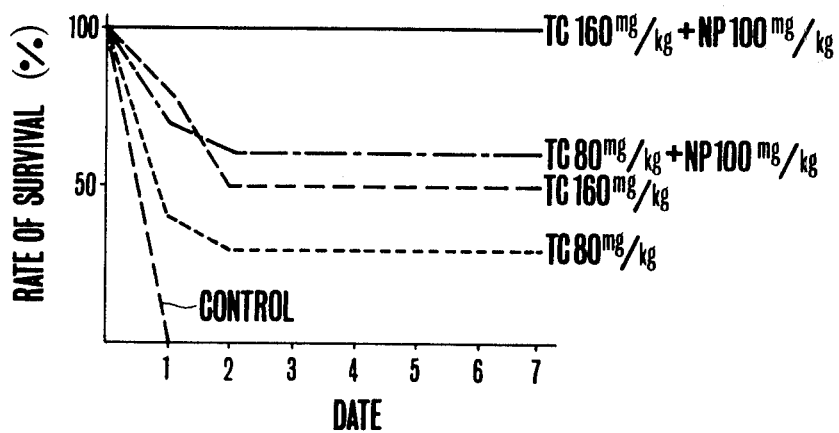

A similar therapeutical test for another bacterial infectious diseases was carried out on five groups of male ICR-JCL mice (each weighing 22±1 g, and each group consisting of 10 mice) by using the tetracycline-resistant strain of *Escherichia coli* and the present substance prepared according to the procedure of Example 1. A quarter milliliter of a Trypto-soy bouillon (see Example 2) suspension, including 5% of mucin, of the tetracycline-resistant bacterial strain prepared as in Example 1 was intraperitoneally inoculated to each mouse. The inoculum was $5 \times 10^8$ bacterial cells per mouse. Two hours after the inoculation, tetracycline was administered orally at the doses of 80 mg/kg (mouse body weight) and 160 mg/kg, respectively, with simultaneous oral administration of the present substance at the dose of 100 mg/kg. The results are shown in FIG. 4 by way of the rate of survival during the 7-day period after the administration. It is apparent from FIG. 4 that combined use of the present substance and tetracycline can produce a far higher remedial effect than when tetracycline is used singly. Also, since much the same effect can be derived from oral administration of the present substance as from its intraperitoneal administration, the present substance can be typified by a broadened scope of use beside its high efficacy.

EXAMPLE 4

Figure 5:
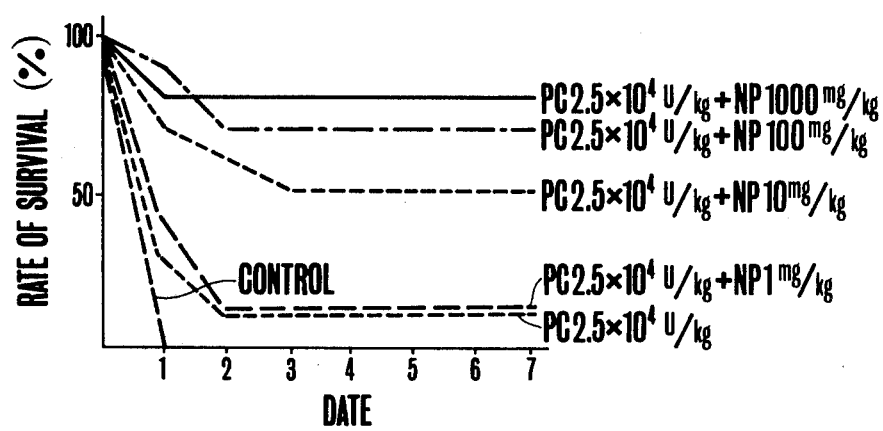

The penicillin G-resistant strain of *Staphylococcus aureus* was inoculated at the rate of $5 \times 10^8$ cells/mouse to five groups (10 mice a group) of male ICR-JCL mice (22±1) according to the procedure of Example 2, followed by intraperitoneal administration of $2.5 \times 10^4$ U/kg of penicillin G and 1, 10, 100 and 1,000 mg/kg of the present substance, respectively to 4 groups (same as used in Example 1). The daily observation of these mice for the period of 7 days after the administration gave the results shown in FIG. 5.

EXAMPLE 5

A similar therapeutical test for infectious diseases was carried out using six groups of male ICR-JCL mice, each group consisting of 10 mice inoculated with $5 \times 10^8$ cells of tetracycline-resistant *Escherichia coli*/mouse by using the procedures in Example 3.

Figure 6:
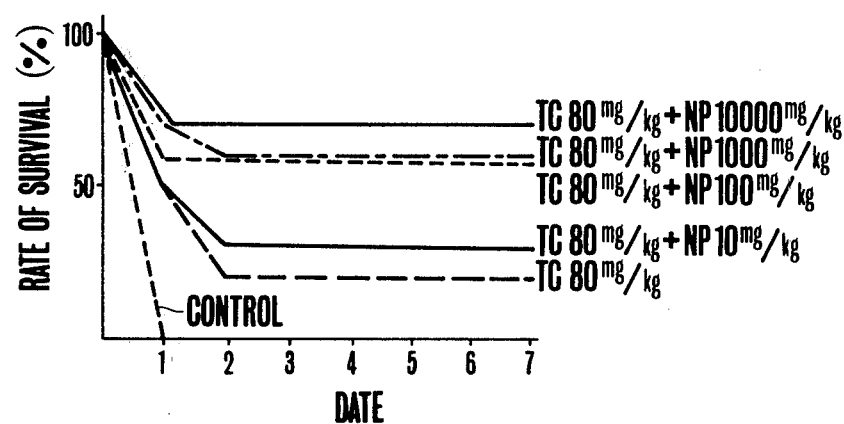

Two hours after the inoculation, tetracycline was administered at the dose of 80 mg/kg (body weight of mouse) with simultaneous oral administration of the present substance used in Example 1 at the respective doses of 0, 10, 100, 1000 and 10,000 mg/kg, the sixth group being control. Observation of the mice was daily carried out until the 7th day and the results obtained during the observation are shown in FIG. 6.

EXAMPLE 6

A strain (CM-151) of *Coriolus hirsutus* (Fr.) Quél. (FERM-P 2711*) was cultured as in Example 1, and then extracted and refined to obtain 17.5 g of powdery substance. The properties of this substance, as determined according to the methods of Example 1, were as follows:

(1) Elementary analysis: 43.7% of carbon, 6.4% of hydrogen, and 5.5% of nitrogen.

(2) Specific rotatory power: $[\alpha]_D^{25} = +30°$ (3) Saccharide composition: 79% of glucose, 15% of mannose, 2% of xylose, 4% of galactose and trace of fucose.

(4) Protein content: 33%

(5) Ratio of saccharide bonds ($\beta/\alpha$): 71/29

*Deposited at the Fermentation Research Insistitute with the deposite number of:

(6) Average molecular weight: 95,000

(7) Composition of protein portion: 15% of aspartic acid, 9% of threonine, 5% of serine, 14% of glutamic acid, 6% of proline, 9% of glycin, 9% of alanine, 7% of valine, 1% of methionine, 5% of isoleucine, 6% of leucine, 2% of tryptophan, 4% of phenylalanine, 2% of lysin, 3% of alginine, 2% of ammonia, 1% of N-glucosamine and each trace of cystine, tyroshine and histidine.

The following experiment was then carried out on the present substance having the above-mentioned properties.

The chloramphenicol-resistant strain of *Salmonella enteritidis* were obtained as in Example 1.

A quarter milli-liter of suspension of the aforementioned chloramphenicol-resistant bacterial strain in Tryptosoy-bouillon (see Example 2) including 5% of mucin was intraperitoneally inoculated to each mouse of 5 groups of male ICR-JCL mouse, the group consisting of 10 mice. The inoculum was $1 \times 10^8$ cells/mouse. Twenty five hours after the inoculation, 50 mg/kg of chloramphenicol was administered intraperitoneally. 500 mg/kg of the present substance was further given orally to another group. The rate of survival 5 days after the administration was 40% in the group where chloramphenicol alone was administered, while it was 80% in the group where the antibiotic was given in combination with the present substance.

EXAMPLE 7

The streptomycin resistant strain of *Klebsiella pneumoniae* was obtained by the procedure of Exampe 1 and 0.25 ml of a Trypto-soy bouillon (see Example 2) containing 5% of mucin and the bacterial strain was intraperitoneally inoculated to each mouse of 2 groups of male ICR-JCL mouse, the group consisting of 10 mice at the rate of $1 \times 10^8$ cells per mouse. Three hours after this inoculation, 100 mg/kg of streptomycin was intraperitoneally administered. Another group was further given 120 mg/kg of the present substance, obtained by the description in Example 6, via intraperitoneal administration. The survival rate 6 days after administration was 50% in the group where streptomycin was used singly, but it was as high as 80% in the group where the present substance was used with streptomycin.

EXAMPLE 8

A quarter milli-liter of a suspension of the colistin-resistant strain of *Pseudomonas aeruginosa* cultured by the same procedure in Example 1 in Trypto-soy bouillon (see Example 2) including 5% of mucin was intraperitoneally inoculated to each mouse of 2 groups of male ICR-JCL mice (body weight: $22 \pm 1$ g, 10 mice a group) at the rate of $1 \times 10^8$ cells/mouse. Two hours after the inoculation, 190 mg/kg (1 $\mu$g=30 U) of colistin was administered intraperitoneally. The present substance obtained by the same procedure as in Example 6 was also orally administered at a dose of 1,500 mg/kg. The rate of survival 6 days after the administration was 40% in the single colistin group and 70% in the group of joint use with the present substance.

EXAMPLE 9

Experiments of therapeutical treatment of animals infected with an erythromycin-resistant bacterial strain were carried out using the present substance, i.e., a nitrogen-containing polysaccharide prepared by the procedures described in Example 1.

A strain of *Streptococcus faecalis* which has been made to be resistant to erythromycin by the procedures described in Example 1 was intraperitoneally inoculated to the two groups of male ICR-JCL mice (one group comprising 10 animals) at a rate of $1 \times 10^9$ cells/mouse, and after 2 hours of the inoculation, 50 mg/kg (body weight) of erythromycin was orally administered to the mice of one group, and a mixture of erythromycin (50 mg/kg) and the present substance (500 mg/kg) was orally administered to the mice of another group.

After keeping the mice under usual conditions for 6 days, the rate of survival of each mouse was observed on 7th day. The results were as follows:

Rate of survival of the group given only erythromycin:

5/10=(50%)

Rate of survival of the group given the mixture of erythromycin and the present substance:

8/10=(80%)

The results show the effectiveness of the combined effect of the present substance and erythromycin in treating the infectious disease caused by a streptomycin-resistant bacterial strain.

EXAMPLE 10

Similar experiments of therapeutical treatment as in Example 9 was performed by using the present substance obtained by the procedures described in Example 1.

A kanamycin-resistant strain of *Shigella sonnei* obtained by the procedures described in Example 1 was intraperitoneally inoculated to the two groups (each group comprising 10 animals) of male ICR-JCL mice at a rate of $1 \times 10^8$ cells/mouse, and after 2 hours of the inoculation, 20 mg/kg of kanamycin was intraperitoneally administered to the mice of one group, and 100 mg/kg of the present substance and 20 mg/kg of kanamycin were almost simultaneously administered to the mice of another group. After keeping the mice under usual conditions for 6 days. Their rate of survival was observed on 7th day. The results were:

Rate of survival of the group given only kanamycin: 3/10=(30%)

Rate of survival of the group given simultaneous administration of kanamycin and the present substance: 7/10=(70%)

The results also show the effectiveness of the combined effect of the present invention, that is, the simultaneous administration of kanamycin and the present substance as a treatment of the infectious disease caused by a kanamycin-resistant bacterial strain.

EXAMPLE 11

Similar experiments of therapeutical treatment as in Example 9 was performed by using the present substance obtained by the procedures described in Example 1.

A cephaloridine-resistant strain of *Proteus mirabilis* obtained by the procedures described in Example 1 was inoculated into male ICR-JCL mice comprising 20 animals at a rate of $5 \times 10^8$ cells/animal. After 2 hours of the inoculation 80 mg/kg of cephalotidine was administered intraperitoneally into each of 10 mice (of 20 mice), and 50 mg/kg of the present substance and 80 mg/kg of cephaloridine were almost simultaneously administered to each of another 10 mice (of 20 mice) intraperitoneally.

After keeping the animals under usual conditions for 6 days, their rate of survival were observed on 7th day to find:

Rate of survival of the mice only given cephaloridine: 6/10=(60%)

Rate of survival of the mice given simultaneous administration of cephaloridine and the present substance: 10/10=(100%)

The results show the effectiveness of the simultaneous administration of the present substance and cephaloridine on the infectious disease cause by a cephaloridine-resistant bacterial strain.

EXAMPLE 12

Similar experiments as in Example 9 were performed using the present substance obtained by the procedures described in Example 1.

An aminobenzylpenicillin-resistant strain of Klebsiella pneumoniae obtained by the procedures described in Example 1 was inoculated intraperitoneally into two groups (one group comprising 10 animals) of male ICR-JCL mice at a rate of $1 \times 10^8$ cells/mouse.

After 2 hours of the inoculation, 100 mg/kg of aminobenzyl penicillin was orally administered to each mouse of one group, and 1,000 mg/kg of the present substance simply admixtured with 100 mg/kg of aminobenzyl penicillin were orally administered to each mouse of another group. After keeping the mice under usual conditions, the rate of survival of each group was observed on 7th day with the results:

Rate of survival of the group given only aminobenzylpenicillin:
4/10=(40%)

Rate of survival of the group given simultaneous administration of the present substance and aminobenzylpenicillin:
9/10=(90%)

EXAMPLE 13

Similar experiments as Example 12 were performed using the present substance prepared by the procedures described in Example 6 in the treatment of infectious disease caused by a strain of Enteribacter aerogenes which has been made to be resistant to aminobenzylpenicillin by the procedures described in Example 1.

The aminobenzylpenicillin-resistant strain of Enterobacter aerogenes was inoculated into two groups (a group comprising 10 animals) of male ICR-JCL mice at a rate of $5 \times 10^8$ cells/mouse intraperitoneally, and after 2 hours of the inoculation, 100 mg/kg of aminobenzylpenicillin were orally administered to one group of the mice, and a simple mixture of 100 mg/kg of aminobenzylpenicillin and 1,000 mg/kg of the present substance was orally administered to another group of the mice.

After keeping the mice for 6 days under usual conditions, their rate of survival was determined on 7th day. The results are:

Rate of survival of the group given only aminobenzylpenicillin:
7/10=(70%) and

Rate of survival of the group given the mixture of the present substance and aminobenzylpenicillin:
10/10=(100%).

As is seen in Examples 9-13, combined administration of the present substance and an antibiotic was always superior than the sole administration of the entibiotic to which the pathogenic bacterial strain has become resistant, in giving a higher rate of survival to animals infected with the bacterial strain resistant to the above-mentioned antibiotic.

What is claimed is:

1. A pharmaceutical composition for the treatment of a bacterial infection due to a strain of a pathogenic bacterial species which has come to be resistant to treatment with conventional antibiotics, which comprises an antibacterially effective amount of an antibiotic and a nitrogen-containing polysaccharide obtainable by extracting mycelia of a fungus belonging to the genus Coriolus from the family Polyporaceae of Basidiomycetes with an aqueous solvent, having a molecular weight of from 5,000 to 300,000, as determined by the ultracentrifugal method and an elementary composition of 42.0 to 46.0% of carbon, 5.3 to 7.0% of hydrogen, 0.5 to 8.0% of nitrogen and the balance of oxygen, easily soluble into water, however, not soluble into acetone, pyridine, chloroform and hexane, showing characteristic absorption bands at 840 cm$^{-1}$ and 890 cm$^{-1}$ in an infrared spectrum, and a specific rotation $[\alpha]_D^{25}$ of 0° to 50° and having a ratio of saccharide portion to protein portion within a range of 62:38 to 97:3 as indicated by proton nuclear magnetic resonance spectroscopy, said antibiotic being capable of combatting said bacterial infectious disease when administered together with said nitrogen-containing polysaccharide.

2. The pharmaceutical composition according to claim 1, wherein said antibiotic is penicilline G.

3. The pharmaceutical composition according to claim 1, wherein said antibiotic is streptomycin.

4. The pharmaceutical composition according to claim 1, wherein said antibiotic is kanamycin.

5. The pharmaceutical composition according to claim 1, wherein said antibiotic is chloramphenicol.

6. The pharmaceutical composition according to claim 1, wherein said antibiotic is tetracycline.

7. The pharmaceutical composition according to claim 1, wherein said antibiotic is erythromycin.

8. The pharmaceutical composition according to claim 1, wherein said antibiotic is aminobenzylpenicillin.

9. The pharmaceutical composition according to claim 1, wherein said antibiotic is cephaloridine.

10. The pharmaceutical composition according to claim 1, wherein said antibiotic is colistin.

11. The pharmaceutical composition according to claim 1, wherein said pathogenic bacterial species of which said strain has become resistant to conventional antibiotics is selected from the group consisting of Staphylococcus aureus, Escherichia coli, Salmonella enteritidis, Klebsiella pneumoniae, Shigella sonnei, Pseudomonas aeruginosa, Streptococcus faecalis, Proteus mirabilis and Enterobacter aerogenes.

12. The pharmaceutical composition according to claim 1, wherein the weight ratio of said nitrogen-containing polysaccharide to said antibiotic is from 1:4 to 10:1.

13. A method for treating a bacterial infection induced by a strain of a bacteria species, which has developed a resistance to a specific antibiotic, which comprises administering to a host in need of such treatment an antibacterially effective amount of an antibiotic in combination with a nitrogen-containing polysaccharide obtainable by extracting mycelia of basidiomycetes belonging to the genus Coriolus of Polyporaceae with an aqueous solvent, said polysaccharide having a molecular weight of from 5,000 to 300,000 as determined by ultracentifugation, containing 42.0 to 46.0% carbon, 5.3 to 7.0% hydrogen and 0.5 and 8.0% nitrogen, having a specific rotatory power of 0° to +50.0°, having good solubility in water but being insoluble in acetone, pyridine, chloroform and hexane, showing characteristic absorption at 840 cm$^{-1}$ and 890 cm$^{-1}$ in the infrared spectrum and having a ratio of saccharide portion to protein portion of from 62/38 to 97/3 as indicated by nuclear magnetic resonance spectroscopy, said antibiotic being capable of combatting said strain of bacteria species when administered with said nitrogen-containing polysaccharide.

14. The method of claim 13, wherein said antibiotic is selected from the group consisting of streptomycin, chloramphenicol, penicillin G, aminobenzylpenicillin, tetracycline, erythromycin, cephaloridine and colistin.

15. The method of claim 13, wherein said strain of a bacteria species belongs to the group consisting of *Staphylococcus aureus, Escherichia coli, Salmonella enteristidis, Klebsiella pneumoniae, Shigella sonnei, Pseudomonas aeruginosa, Streptococcus faecalis, Proteus mirabilis* and *Enterobacter aerogenes.*

* * * * *